US011672476B2

(12) United States Patent
Bodner

(10) Patent No.: US 11,672,476 B2
(45) Date of Patent: Jun. 13, 2023

(54) INTRATHECAL CATHETER WITH MEANS TO MEASURE QUALITY OF DRUG DISPERSION

(71) Applicant: Medtronic, Inc., Minneapolis, MN (US)

(72) Inventor: Jeffrey Bodner, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 464 days.

(21) Appl. No.: 16/572,872

(22) Filed: Sep. 17, 2019

(65) Prior Publication Data
US 2021/0077016 A1 Mar. 18, 2021

(51) Int. Cl.
*A61B 5/00* (2006.01)
*A61B 5/01* (2006.01)
(Continued)

(52) U.S. Cl.
CPC ............ *A61B 5/4848* (2013.01); *A61B 5/015* (2013.01); *A61B 5/055* (2013.01);
(Continued)

(58) Field of Classification Search
CPC ....... A61B 5/4848; A61B 5/015; A61B 5/055; A61B 5/14507; A61B 5/407; A61B 5/742;
(Continued)

(56) References Cited

U.S. PATENT DOCUMENTS

| 4,502,488 A | 3/1985 | Degironimo et al. |
| 4,730,623 A | 3/1988 | Lee |

(Continued)

FOREIGN PATENT DOCUMENTS

| EP | 0226220 A2 | 6/1987 |
| EP | 1345640 B1 | 8/2007 |

(Continued)

OTHER PUBLICATIONS

K. Tangen, I. Nestorov, A. Verma, J. Sullivan, R. W. Holt and A. A. Linninger, "In Vivo Intrathecal Tracer Dispersion in Cynomolgus Monkey Validates Wide Biodistribution Along Neuraxis," in IEEE Transactions on Biomedical Engineering, vol. 6, pp. 1122-1132, Apr. 2020 (Year: 2019).*

(Continued)

*Primary Examiner* — Colin T. Sakamoto
*Assistant Examiner* — Tommy T Ly
(74) *Attorney, Agent, or Firm* — Patterson Thuente, P.A.

(57) ABSTRACT

A method of determining a local cerebrospinal fluid flow rate. The method including the steps of positioning a distal end of the catheter in a flow of cerebrospinal fluid of the patient, the catheter including an infusion port and at least one temperature sensor positioned at a fixed distance from the infusion port, infusing a bolus of a temperature controlled fluid through the infusion port into the flow of cerebrospinal fluid, and monitoring a temperature sensed by the at least one temperature sensor, wherein a change in the temperature sensed by the at least one temperature sensor over time is representative of a local cerebrospinal fluid flow rate in proximity to the infusion port.

20 Claims, 7 Drawing Sheets

(51) Int. Cl.
*A61M 5/00* (2006.01)
*A61B 5/055* (2006.01)
*A61B 5/145* (2006.01)

(52) U.S. Cl.
CPC .......... *A61B 5/14507* (2013.01); *A61B 5/407* (2013.01); *A61B 5/742* (2013.01); *A61M 5/007* (2013.01)

(58) Field of Classification Search
CPC ....... A61B 5/4064; A61B 8/12; A61B 5/4566; A61B 5/028; A61M 5/007; A61M 2202/0464; A61M 2205/3379; A61M 5/16836; A61M 5/1723; A61M 5/427; A61M 27/006; A61M 5/1452
See application file for complete search history.

(56) References Cited

U.S. PATENT DOCUMENTS

| | | | |
|---|---|---|---|
| 5,897,528 | A | 4/1999 | Schultz |
| 5,931,805 | A | 8/1999 | Brisken |
| 6,013,051 | A | 1/2000 | Nelson |
| 7,192,414 | B2 | 3/2007 | Stultz |
| 7,438,701 | B2 | 10/2008 | Theeuwes et al. |
| 7,593,770 | B2 | 9/2009 | Lemer |
| 9,655,528 | B2 | 5/2017 | Zhu |
| 9,682,193 | B2 | 6/2017 | Anand et al. |
| 2001/0044588 | A1* | 11/2001 | Mault ................ A61B 5/14532 600/549 |
| 2006/0178617 | A1 | 8/2006 | Adams et al. |
| 2007/0073250 | A1 | 3/2007 | Schneiter |
| 2007/0137296 | A1 | 6/2007 | Krivitski et al. |
| 2008/0146990 | A1 | 6/2008 | Jenson et al. |
| 2008/0194940 | A1* | 8/2008 | Groth ..................... A61B 6/507 600/407 |
| 2010/0125246 | A1 | 5/2010 | Kalpin et al. |
| 2010/0324397 | A1* | 12/2010 | Purdy ................ A61M 25/0662 600/378 |
| 2012/0302938 | A1 | 11/2012 | Bowd et al. |
| 2013/0109998 | A1* | 5/2013 | Swoboda ................ G01F 1/684 600/549 |
| 2013/0324892 | A1 | 12/2013 | Zhu et al. |
| 2014/0228765 | A1 | 8/2014 | Burke et al. |
| 2015/0305629 | A1* | 10/2015 | Fritz ........................ A61B 5/01 600/549 |
| 2016/0113699 | A1* | 4/2016 | Sverdlik ............ A61B 18/1492 606/27 |
| 2016/0331897 | A1 | 11/2016 | Anand et al. |
| 2018/0185058 | A1* | 7/2018 | Anand ................ A61M 5/3286 |
| 2018/0280598 | A1* | 10/2018 | Curran ................ A61M 60/205 |
| 2019/0160254 | A1 | 5/2019 | Anand et al. |
| 2020/0125246 | A1 | 4/2020 | Stephens et al. |

FOREIGN PATENT DOCUMENTS

| | | | | |
|---|---|---|---|---|
| WO | WO-2004100769 | A2 * | 11/2004 | ......... A61K 49/0017 |
| WO | WO-2006002275 | A2 * | 1/2006 | .......... A61M 39/223 |
| WO | WO-2017122199 | A1 * | 7/2017 | ........... A61B 5/4857 |
| WO | WO-2018005169 | A1 * | 1/2018 | ........ A61M 25/0026 |
| WO | WO2018119179 | A1 | 6/2018 | |
| WO | WO-2019173784 | A1 * | 9/2019 | ......... A61B 17/3401 |

OTHER PUBLICATIONS

Office Action for EP Application No. 19179065.8, dated Sep. 10, 2020, 6 pages.
International Search Report and Written Opinion for PCT/US2020/043252, dated Sep. 30, 2020, 12 pages.
International Search Report and Written Opinion for PCT /US2020/043249, dated Nov. 16, 2020, 10 pages.

* cited by examiner

INTRATHECAL CATHETER WITH MEANS TO MEASURE QUALITY OF DRUG DISPERSION

TECHNICAL FIELD

The present technology is generally related to implantable medical devices, and more particularly to a system and method utilizing an implantable catheter to quantify drug dispersion within the cerebrospinal fluid of a patient.

BACKGROUND

Administration of prescribed therapeutic agents, nutrients, drugs, and medicaments such as antibiotics, blood clotting agents, analgesics and other fluid and/or fluid like substances (collectively "medicaments" or "infusates") directly into the cerebrospinal fluid of a patient has a number of important advantages over other forms of medicament administration. For example, oral administration is often not workable because the systematic dose of the substance needed to achieve the therapeutic dose at the target site may be too large for the patient to tolerate without adverse side effects. Also, some substances simply cannot be absorbed in the gut adequately for a therapeutic dose to reach the target site. Moreover, substances that are not lipid soluble may not cross the blood-brain barrier adequately if needed in the brain.

Because of these advantages, administration of medicaments directly into the cerebrospinal fluid of a patient is the preferred option for treating a number of diseases and disorders; particularly those that require regular chronic (i.e. long-term) pharmacological intervention, including tremor, spasticity, multiple sclerosis, Alzheimer's disease, Parkinson's disease, amyotropic lateral sclerosis (ALS), Huntington's disease, cancer, epilepsy, chronic pain, urinary or fecal incontinence, sexual dysfunction, obesity, and gastroparesis, to name just a few.

Presently, intrathecal delivery techniques rely on a natural flow of the cerebrospinal fluid for medicament dispersion. Proper dispersion of the medicament into the cerebrospinal fluid is largely dependent on the presence of a good flow of cerebrospinal fluid at the location of infusion. Unfortunately, the flow rate of the cerebrospinal fluid within the intrathecal space of a given patient may vary significantly based on the patient's anatomy; some areas in the intrathecal space may have a high flow rate, while other areas may have a low flow rate. As patient anatomies differ, it is further believed that areas with higher cerebrospinal fluid flow rates may vary from patient to patient.

Today few options exist for determining the cerebrospinal fluid flow rate at an intended infusion site. One method that has been used is the injection of a contrast agent into the cerebrospinal fluid while subjecting the patient to magnetic resonance imaging (MM). Although this method is feasible, because it is both expensive and time-consuming, it does not lend itself to frequent clinical use. Moreover, the results produced by the method are not easily interpreted by all clinicians. As a result, clinicians presently do not have a good mechanism to determine whether an intended implant location for an intrathecal catheter is in an area of good cerebrospinal flow. Unknowingly positioning an intrathecal catheter in an area with low cerebrospinal fluid flow may result in suboptimal treatment.

The present disclosure addresses this concern.

SUMMARY OF THE DISCLOSURE

The techniques of this disclosure generally relate to a catheter with an integrated temperature sensor configured to measure the mixing of a temperature control fluid with the cerebrospinal fluid near an intended intrathecal infusion site to determine a quality of the dispersion of a medicament within the cerebrospinal fluid. For example, in one embodiment, a cold bolus of saline can be infused into the intrathecal space, and the time it takes to affect a change in temperature as measured by an integrated temperature sensor can be an indication of the quality of the anticipated drug dispersion. In some embodiments, multiple measurements can be made to map the intrathecal space before selecting a final infusion site, thereby optimizing the therapeutic effect of medicament infusion into the cerebrospinal fluid of a patient. Accordingly, embodiments of the present disclosure present a relatively inexpensive, easily manufactured device configured to directly measure cerebrospinal fluid flow rates to achieve improved medicament dispersion and better clinical outcomes.

One embodiment of the present disclosure provides a method of determining a local cerebrospinal fluid flow rate. The method can include: positioning a distal end of the catheter in a flow of cerebrospinal fluid of the patient, the catheter including an infusion port and at least one temperature sensor positioned at a fixed distance from the infusion port; and infusing a bolus of a temperature controlled fluid through the infusion port into the flow of cerebrospinal fluid; and monitoring the temperature sensed by the at least one temperature sensor, wherein a change in the temperature sensed by the at least one temperature sensor overtime is representative of a local cerebrospinal fluid flow rate in proximity to the infusion port.

In one embodiment, the temperature controlled fluid can be a saline solution. In one embodiment, the temperature controlled fluid can be chilled, having a temperature in a range of between about 35° F. and about 46° F. In one embodiment, the temperature controlled fluid can be heated, having a temperature in a range of between about 99° F. and about 150° F. In one embodiment, the temperature controlled fluid can be a contrast agent visible through magnetic resonance imaging (MRI). In one embodiment, the bolus of temperature controlled fluid can be infused via a syringe pump.

In one embodiment, the method further includes graphically displaying the temperature sensed by the at least one temperature sensor over a period of time. In one embodiment, the period of time has a predefined duration of between about 10 seconds and about 300 seconds. In one embodiment, the method further includes repeating the method at a different location within the intrathecal space of the patient to determine a local cerebrospinal flow rate at the different location.

Another embodiment of the present disclosure provides a method of mapping a fluid flow rate within the cerebrospinal fluid of the patient. The method can include: inserting an intrathecal catheter into a patient, the intrathecal catheter having a distal end configured to be positioned within a flow of cerebrospinal fluid, a proximal end, and a body defining a lumen extending lengthwise along the catheter configured to enable a delivery of a bolus of a temperature controlled fluid from the proximal end to an infusion port positioned in proximity to the distal end, the intrathecal catheter further including at least one temperature sensor positioned at a fixed distance from the infusion port; infusing a bolus of a temperature controlled saline solution through the infusion port into the flow of cerebrospinal fluid; and monitoring a temperature sensed by the at least one temperature sensor over a duration of time between about 10 seconds and about 300 seconds, wherein a change in the temperature sensed by the at least one temperature sensor over time is representative of a local cerebrospinal fluid flow rate in proximity to the infusion port.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Another embodiment of the present disclosure provides a medical device configured to determine a local cerebrospinal fluid flow rate. The medical device can include a catheter and a processor. The catheter can have a distal end configured to be positioned within a flow of cerebrospinal fluid of the patient, a proximal end, and a body defining a lumen extending lengthwise along the catheter configured to enable a delivery of a bolus of a temperature controlled fluid from the proximal end to an infusion port positioned in proximity to the distal end. The catheter can further include at least one temperature sensor positioned at a fixed distance from the infusion port. The processor can be configured to receive and process data sensed by the at least one temperature sensor over a period of time to determine the velocity of the temperature controlled fluid exiting the infusion port, wherein the velocity of the temperature controlled fluid is representative of a flow rate of the cerebrospinal fluid in proximity to the infusion port.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

Figure 1:
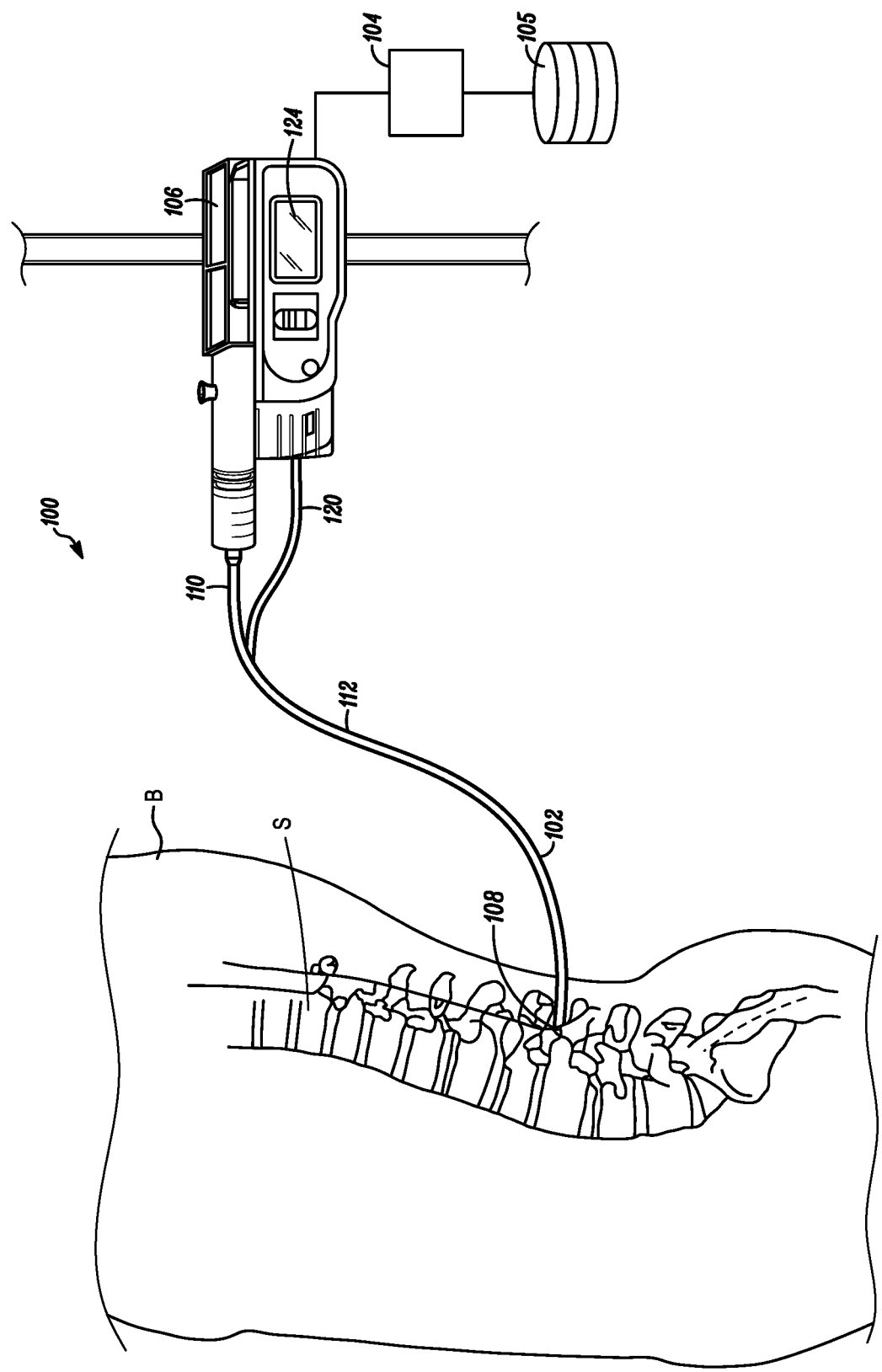
FIG. 1 is a schematic diagram depicting a medical device configured to determine a local cerebrospinal flow rate, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, a medical device 100 configured to measure the mixing of a temperature-controlled fluid with the cerebrospinal fluid near an intended intrathecal infusion site to determine a quality of an anticipated intrathecal medicament delivery is depicted in accordance with an embodiment of the disclosure. The medical device 100 can include a catheter 102 and an optional processor 104 and memory 105, which in some embodiments can double as an infusion pump 106. In some embodiments, a distal tip 108 of the catheter 102 can be inserted within the subarachnoid space of a spine S in the body B of a patient.

Figure 2:
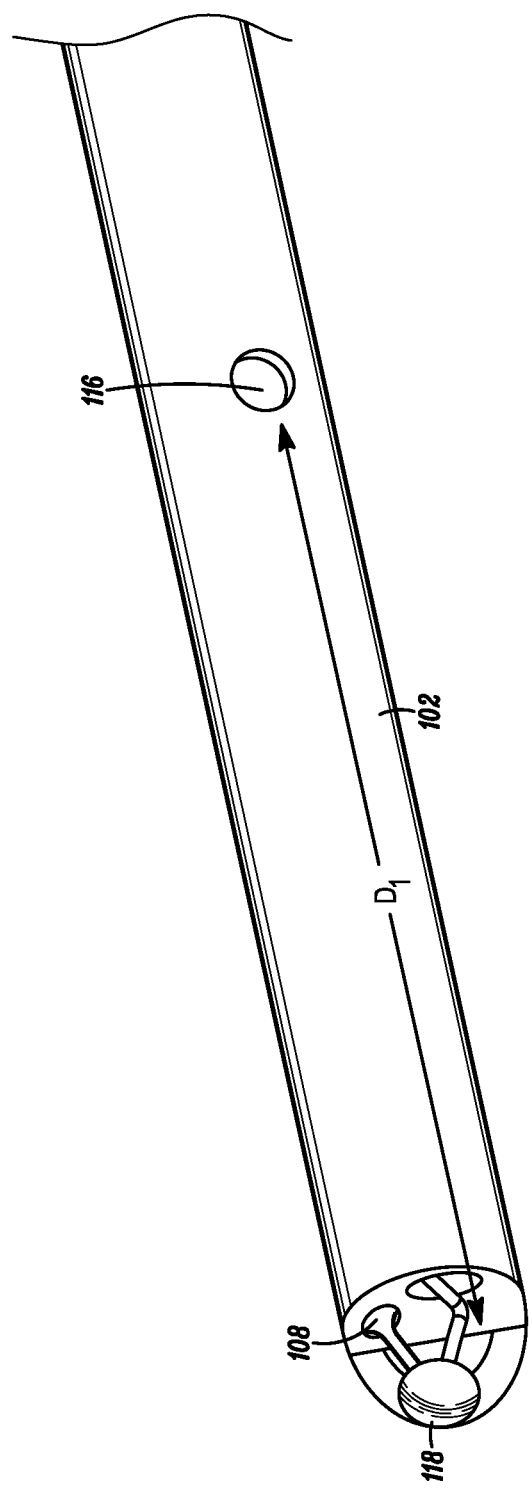
FIG. 2 is a partial, perspective view depicting a portion of a catheter, in accordance with an embodiment of the disclosure.
Figure 3A:
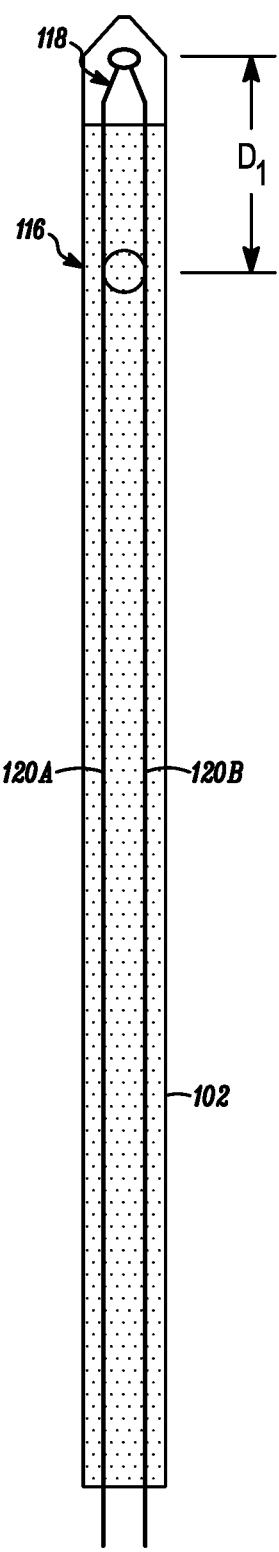
FIG. 3A is a lengthwise sectional view depicting a catheter, in accordance with an embodiment of the disclosure.
Figure 3B:
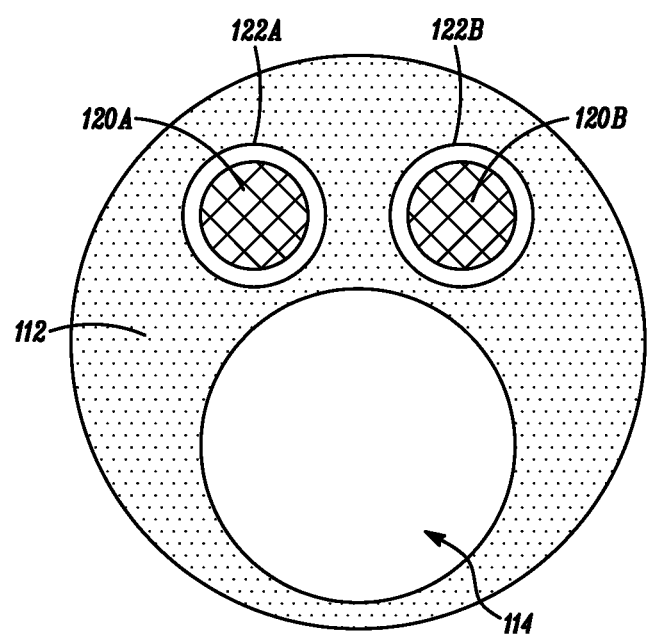
FIG. 3B is a crosswise sectional view depicting the catheter of FIG. 3A.

With additional reference to FIG. 2, a close-up, partial perspective view of the catheter 102 is depicted in accordance with an embodiment of the disclosure. FIGS. 3A-B provide cross-sectional views of the catheter 102 in accordance with an embodiment of the disclosure. The catheter 102 can generally include a distal end 108 configured to be positioned within a flow of cerebrospinal fluid of the patient, a proximal end 110, and a body 112 defining a lumen 114 (as depicted in FIG. 3B) extending lengthwise along the catheter 102. The lumen 114 can be configured to enable a delivery of fluid from the proximal end 110 to an infusion port 116 positioned in proximity to the distal end 108, as well as a withdrawal of fluid from the infusion port 116 to the proximal end 110 of the catheter 102. In some embodiments, the catheter 102 can be a single use transcutaneous catheter. In other embodiments, the catheter 102 can be a surgically-implantable subcutaneous catheter.

With continued reference to FIG. 2, in one embodiment, the catheter 102 can further include at least one temperature sensor 118 positioned a fixed distance $D_1$ from the infusion port 116. For example, in some embodiments, the temperature sensor 118 can be positioned between about 5 mm and about 10 mm from the infusion port 116; although other distances $D_1$ are also contemplated. The temperature sensor 118 can be any sensor configured to detect or sense a change in the temperature of a fluid, for example, a thermocouple or thermistor; although other types of temperature sensors are also contemplated. In some embodiments, the catheter 102 can include two or more of temperature sensors 118 positioned lengthwise along the catheter 102.

In some embodiments, the temperature sensor 118 can be in electrical communication with the processor 104. For example, in one embodiment, one or more electrical conduit 120 extending lengthwise along the catheter 102 parallel to the lumen 114 can electrically couple the temperature sensor 118 to the processor 104. As depicted in FIG. 3B, in one embodiment, the body 112 of the catheter 102 can further define one or more electrical conduit lumens 122A/B through which the one or more electrical conduits 120A/B can traverse. Accordingly, in some embodiments, the catheter 102 can have a tri-lumen configuration, including the first lumen 114, through which fluid can pass, and a second and third lumen 122A/B configured to house the temperature sensor cables or wires 120A/B. In other embodiments, the temperature sensor 118 can be in wireless communication with the processor 104.

Figure 4A:
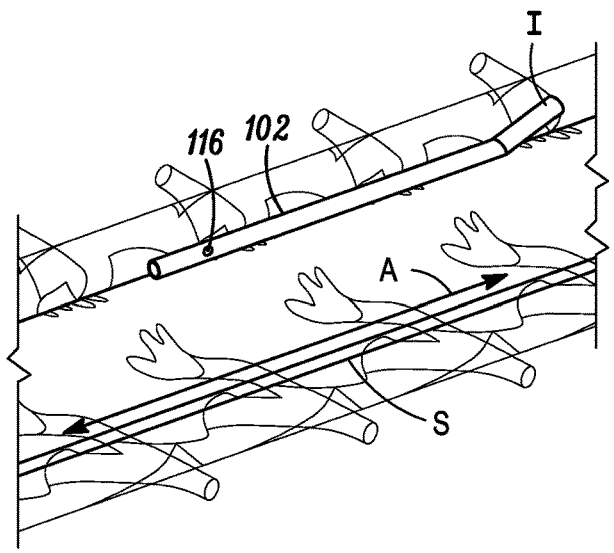
FIG. 4A is a perspective view depicting a catheter inserted into a subarachnoid space of a patient, in accordance with an embodiment of the disclosure.
Figure 4B:
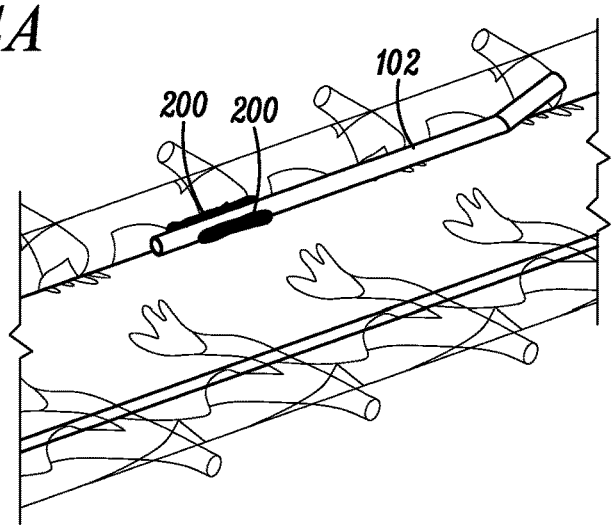
FIG. 4B depicts the dispersion of fluid within the cerebrospinal fluid of the patient after approximately 7.5 seconds of initiating infusion from the catheter of FIG. 4A.
Figure 4C:
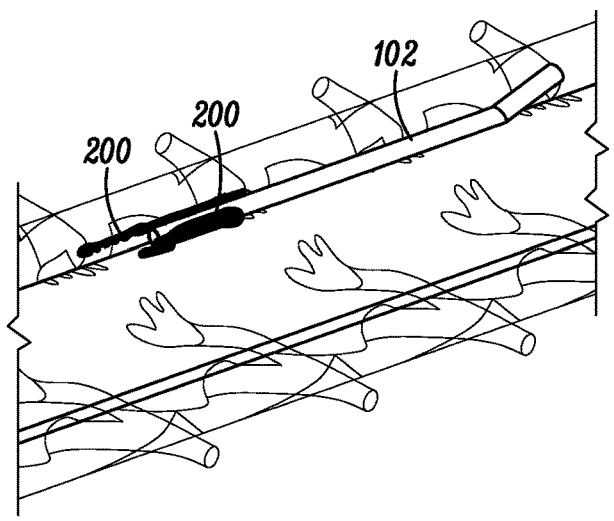
FIG. 4C depicts dispersion of fluid within the cerebrospinal fluid of the patient after approximately 15 seconds of initiating infusion from the catheter of FIG. 4A.

FIG. 4A depicts a catheter 102 positioned within a subarachnoid space of the patient. In particular, the catheter 102 enters the subarachnoid space at an insertion site I, and extends substantially parallel to a longitudinal axis A of the patient's spinal column S, thereby enabling delivery of a fluid 200 through an infusion port 116 of the catheter 102. FIGS. 4B and 4C depict the catheter 102 as the fluid 200 exits the infusion port 116 and flows into the subarachnoid space. Specifically, FIG. 4B depicts a theoretical dispersion of fluid 200 after approximately 7.5 seconds of initiating infusion, and FIG. 4C depicts a theoretical dispersion of fluid 200 after approximately 15 seconds of initiating infusion.

The dispersion of fluid 200 delivered by a catheter 102 into the subarachnoid space (and other areas within the human body) can be simulated using fluid dynamics modeling methods such as finite volume, finite element, or finite difference techniques for finding approximate solutions to systems involving partial equations. In the case of intrathecal delivery, the system of partial differential equations that can model conservation of mass and momentum, also known as Navier-Strokes equations, can simulate cerebrospinal fluid flow. To be more precise, the equations for laminar, oscillating flow of an incompressible fluid with properties similar to water at body temperature can be used to simulate fluid 200 delivery scenarios. Fluid 200 dispersion can further be modeled using various techniques including the Eulerian passive scaler approach or the Lagrangian particle approach.

As depicted in FIGS. 4A-C, when the fluid 200 exits the infusion port 116 and flows into the subarachnoid space, the fluid 200 begins mixing with the cerebrospinal fluid. Where the fluid 200 is expelled from the infusion port at a relatively slow rate (e.g., a flow rate of 1 mL per hour) the fluid 200 may have a tendency to stagnate in the slow-moving cerebrospinal fluid immediately surrounding the catheter. Thereafter, a natural pulsatile flow of the cerebrospinal fluid eventually causes the fluid 200 to drift away from the catheter 102 into faster moving cerebrospinal fluid. Proper mixing of the fluid 200 into the cerebral spinal fluid can take several minutes. A slow or delayed mixing of the medicament with the cerebrospinal fluid can decrease the efficacy of medicament treatments, as well as the resultant therapeutic effects.

Unfortunately, the flow rate of cerebrospinal fluid within the intrathecal space of a given patient may vary significantly based on the patient's anatomy. That is, some areas in the intrathecal space may have a high cerebrospinal fluid flow rate (with desirable medicament mixing qualities), while other areas may have a low cerebrospinal fluid flow rate (with undesirable medicament mixing qualities). As patient anatomies differ, it is further believed that areas with higher cerebral fluid flow rates may vary from patient to patient. As few options exist for determining the cerebrospinal fluid flow rate, most intrathecal catheters are positioned without knowing the flow rate of the cerebrospinal fluid at the intended infusion site. Unknowingly positioning an intrathecal catheter 102 in an area with low cerebrospinal flow may result in a less than ideal treatment outcome, and certainly results in less than optimal mixing of infusate.

Embodiments of the present disclosure enable the mixing of a temperature controlled fluid with the cerebrospinal fluid near an intended intrathecal infusion site to determine a quality of the dispersion of the medicament within the cerebrospinal fluid. For example, in one embodiment, a cold or warm bolus of fluid can be infused into the intrathecal space. The time it takes to affect a change in temperature as measured by the temperature sensor 118 can be an indication of the quality of the anticipated medicament dispersion. Given the direct link between mass transfer (which governs transports of medicament within the intrathecal space) and heat transfer (which is utilized by the temperature sensor 118 to monitor mixing of the medicament with the cerebrospinal fluid), embodiments of the present disclosure directly measure intrathecal dispersion through well understood physical principles.

For example, in one embodiment, after positioning the distal end 108 of the catheter 102 into a flow of the cerebrospinal fluid of the patient, a bolus of chilled fluid can be infused through the infusion port 116 into the flow of cerebrospinal fluid, while monitoring a temperature with the temperature sensor 118. As the chilled fluid mixes with the cerebrospinal fluid, the temperature of the cerebrospinal fluid and later mixture of the chilled fluid and cerebrospinal fluid (as measurable via the temperature sensor 118) will decrease. Accordingly, a temperature change sensed by the temperature sensor 118 is a positive indication that some mixing of the chilled fluid with the cerebrospinal fluid has taken place. Given the fixed distance $D_1$ between the temperature sensor 118 and the infusion port 116, the time over which the temperature changes and the magnitude of the change can be considered representative of the local cerebrospinal flow rate in proximity to the infusion port 116.

Figure 5:
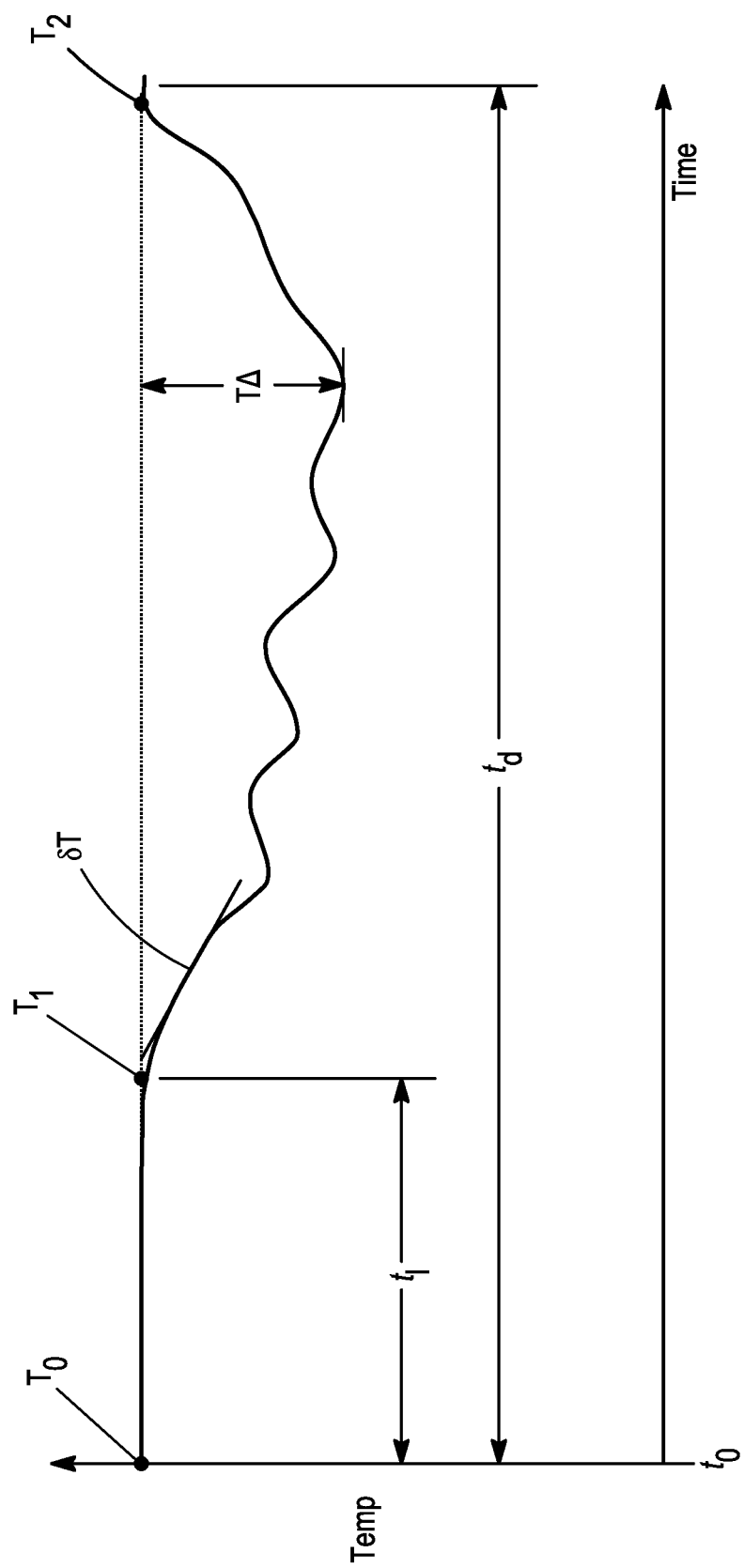
FIG. 5 is a graphical representation depicting the measured temperature at a local infusion site over a dispersion time.

Referring again to FIG. 1, in some embodiments, the processor 104 can include a display 124 configured to display the temperature sensed by the at least one temperature sensor 118. In some embodiments, the displayed temperature can be represented as a digital readout of the temperature. In other embodiments, the temperature sensed by the temperature sensor 118 can be graphically represented over a period of time during which the temperature of the cerebrospinal fluid is monitored. For example, as depicted in FIG. 5, a graphical representation of the temperature (T) sensed by the temperature sensor 118 over a dispersion time ($t_d$) is depicted in accordance with an embodiment of the disclosure. The dispersion time $t_d$ can vary based on the anticipated mixing. For example, in one embodiment, dispersion time $t_d$ can have a predefined duration of between about 30 seconds and about 300 seconds; although other durations of time are also contemplated.

With continued reference to FIG. 5, prior to infusion of the fluid 200, the temperature ($T_0$) sensed by the temperature sensor 118 is of a relatively constant baseline temperature representative of the unmixed cerebrospinal fluid. The infusion of temperature controlled fluid 200 can begin at an initial time ($t_0$) and can continue for a predetermined length of time, which may but need not correspond to the dispersion time $t_d$. The fluid 200 can be any temperature controlled fluid, for example a chilled saline solution maintained in a temperature range of between about 35° F. (2.2° C.) and about 46° F. (7.7° C.); although other types of temperature-controlled fluids and temperature ranges are also contemplated. For example, in another embodiment, the chilled fluid can be a contrast agent, thereby enabling the use of magnetic resonance imaging as an additional aid in surveying the fluid flow within the cerebrospinal fluid of the patient.

It is expected that the temperature sensed by the temperature sensor 118 will remain at the baseline temperature $T_0$ even after infusion of the temperature controlled fluid into the cerebrospinal fluid begins and for a short period of time ($t_1$) thereafter until enough of the fluid 200 has mixed with the surrounding cerebrospinal fluid to lower the temperature of the mixture of fluid 200 and cerebrospinal fluid. As the mixing between the fluid 200 and the cerebrospinal fluid is largely affected by a natural flow of the cerebrospinal fluid, the duration of time $t_1$ (alternatively referred to as initial dispersion time) is indicative of the cerebrospinal fluid flow rate. Specifically, the time $t_1$ represents the velocity of the fluid 200 as it traverses the distance D1 between the infusion port 116 and the temperature sensor 118 over the initial dispersion time $t_1$. A relatively longer initial dispersion time $t_1$ is indicative of a slower cerebral spinal fluid flow rate, while a relatively shorter initial dispersion time $t_1$ is indicative of a faster cerebral spinal fluid flow rate. Naturally, a faster cerebral spinal fluid flow rate is desirable, as it promotes a more rapid dispersion of medicament within the cerebrospinal fluid.

Accordingly, at time $t_1$ the temperature (T1) sensed by the temperature sensor 118 begins to decrease to reflect the temperature of the mixture of the fluid 200 and cerebrospinal fluid. Thereafter, the temperature sensed by the temperature sensor 118 may fluctuate based on the natural pulsatile flow of the cerebrospinal fluid until it returns to a final temperature (T2) representative of the baseline temperature of the unmixed cerebrospinal fluid. The rate ($\delta T$) at which the temperature decreases and the maximum difference in temperature ($T_A$) can also be indicative of the cerebrospinal fluid flow rate. For example, a steeper rate $\delta T$ at which the temperature decreases can represent a faster and more thorough mixing of the fluid 200 with the cerebrospinal fluid. Likewise, a larger temperature differential $T_A$ can represent a faster and more thorough mixing of the fluid 200 with the cerebrospinal fluid.

Figure 6A:
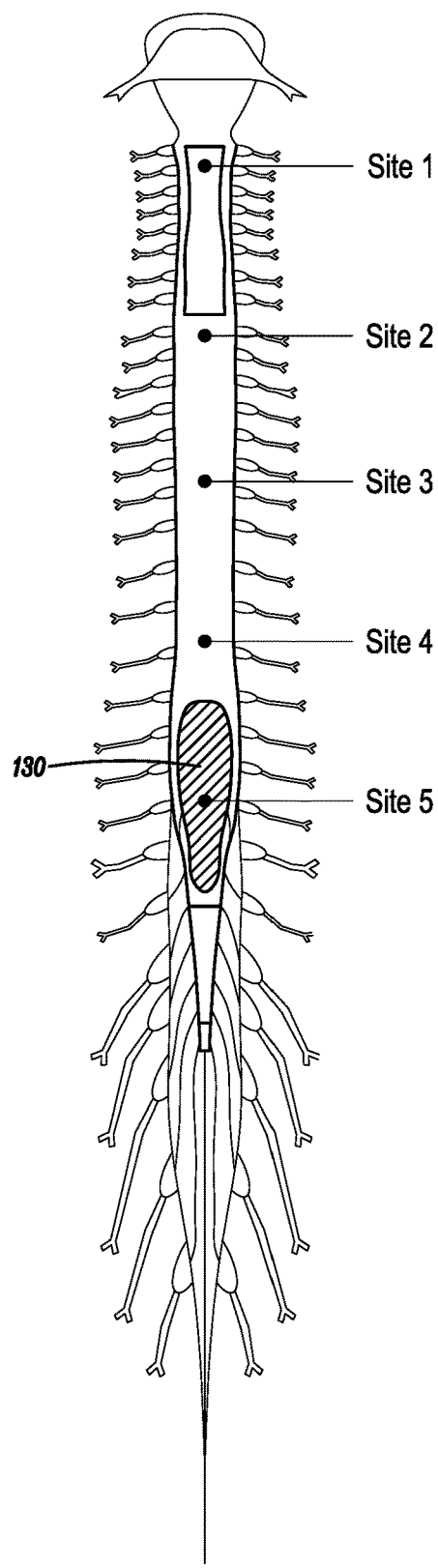
FIG. 6A is a graphical representation depicting a plan view map of the intrathecal space of a patient representing cerebrospinal fluid flow rates, in accordance with an embodiment of the disclosure.
Figure 6B:
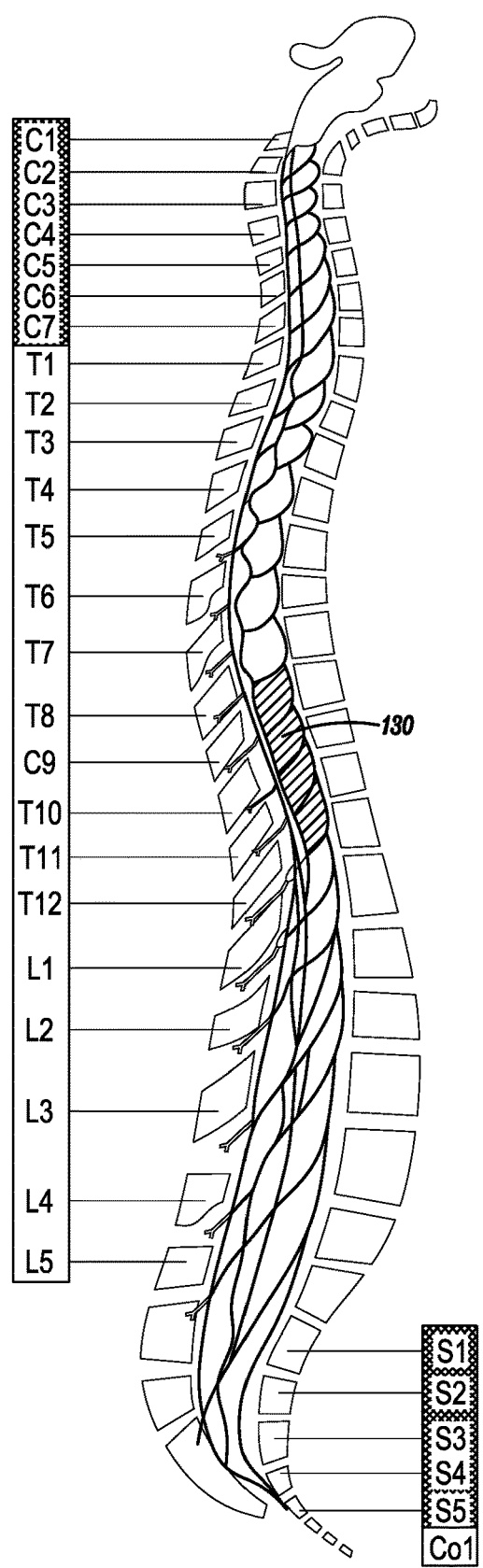
FIG. 6B is a graphical representation depicting a profile view map corresponding to the plan view map of FIG. 6A.

In some embodiments, multiple measurements along the spine S of a patient to map the intrathecal space can be made before selecting a final infusion site, thereby enabling the selection of an optimal site for medicament infusion to maximize the therapeutic effect of the treatment. With additional reference to FIGS. 6A-B, in one embodiment, the medical device or system 100 can be configured to receive sensor data from a plurality of localized sites (Sites$_{1-5}$) to aid in the determination of an optimal infusion site 130. For example, as depicted in FIGS. 6A-B, in one embodiment, the processor 104 can utilize data from the plurality of localized sites (Sites$_{1-5}$) to create a map of the intrathecal space to represent cerebrospinal fluid flow rates therewithin. In some embodiments, the processor 104 can interpolate points between the localized sites (Sites$_{1-5}$) to create a heat map type graphical representation of the fluid flow rates within a patient's cerebrospinal fluid, thereby identifying the one or more optimal sites 130 to position an intrathecal catheter for infusion of medicament. Other types of graphical representations of the flow rates within the cerebrospinal fluid are also contemplated.

Figure 7:
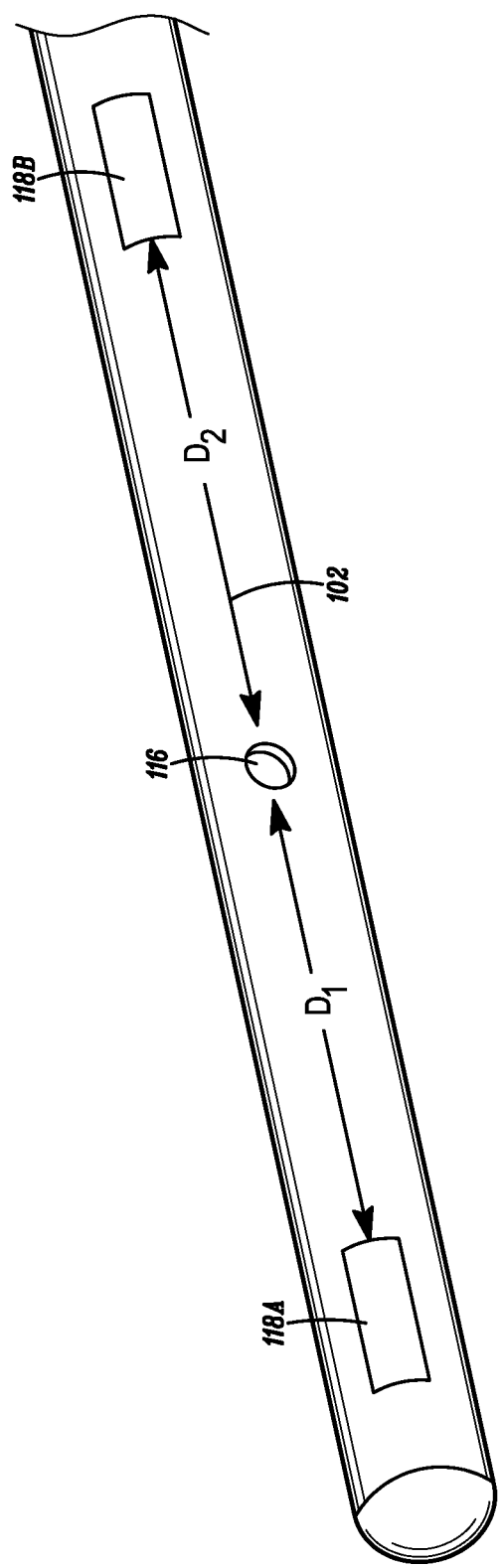
FIG. 7 is a partial, perspective view depicting a portion of a catheter having two or more temperature sensors, in accordance with an embodiment of the disclosure.

With reference to FIG. 7, in some embodiments, the catheter 102 can include at least a first temperature sensor 118A and a second temperature sensor 118B, respectively positioned fixed distances $D_1$ and $D_2$ on either side of the infusion port 116, thereby enabling the determination of a fluid flow direction, as well as a fluid velocity and mass flow rate. For example, as a flow of chilled fluid flows out of the infusion port 116 and begins mixing with the surrounding cerebrospinal fluid, a change in temperature of the fluid mixture can be sensed by either or both of the first temperature sensor 118A and the second temperature sensor 118B. A shorter initial dispersion time or greater maximum difference in temperature by either of the first or second temperature sensor 118A/B can be an indication of the fluid flow direction. In other embodiments, the first and second temperature sensors 118A-B can be positioned on the same side of the infusion port 116.

In one embodiment, the first temperature sensor 118A can be positioned in close proximity to the infusion port 116 to detect when the chilled fluid begins flowing out of the infusion port 116, thereby providing a precise point in time to treat as the start of the infusion, rather than relying on a calculated infusion start time.

Accordingly, the present disclosure provides a relatively inexpensive, easily manufactured catheter 102 that can be configured to directly measure cerebrospinal flow rates to achieve improved medicament dispersion and better clinical outcomes. As an aid in reducing costs, in some embodiments, the catheter 102 can be compatible with a variety of conventionally available processors 104 and infusion pumps 106. For example, in one embodiment, the processor 104 can be a relatively inexpensive digital display, such as a multimeter configured to display the temperature sensor 118 output (e.g., a temperature, voltage, current, resistance, etc.). The infusion pump 106 can be a syringe pump, available from a variety of manufacturers.

In other embodiments, the system 100 can include a more complex processor 104 or combination processor-infusion pump 104/106 with cerebrospinal fluid flow calculation and/or cerebrospinal fluid mapping capabilities. In yet other embodiments, the system 100 can include an implantable pump having an access port through which the temperature controlled fluid 200 can be administered to check patency of the catheter and/or to periodically monitor cerebrospinal fluid flow conditions of the localized site in which the catheter 102 is positioned.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method for determining a suitable location for delivery of a medicament into a cerebrospinal fluid of a patient, the method comprising:
    positioning a distal end of a catheter at a location in the cerebrospinal fluid of the patient, the distal end of the catheter defining an infusion port and comprising at least one temperature sensor positioned at a fixed distance from the infusion port;
    infusing a bolus of a temperature-controlled fluid through the infusion port into the cerebrospinal fluid, wherein the temperature-controlled fluid does not comprise the medicament;
    monitoring, via the at least one temperature sensor at the distal end of the catheter, a change in a temperature of a mixture of the bolus of the temperature-controlled fluid and the cerebrospinal fluid;
    determining, based on the change in the temperature of the mixture, a flow rate of the cerebrospinal fluid;
    determining, based on the flow rate of the cerebrospinal fluid, an estimated quality of a potential dispersion of the medicament into the cerebrospinal fluid by the catheter at the location; and
    outputting for display an indication of the estimated quality of the potential dispersion at the location.

2. The method of claim 1, wherein the temperature-controlled fluid comprises a saline solution.

3. The method of claim 1, wherein the temperature-controlled fluid has a bolus temperature of between about 35° F. to about 46° F.

4. The method of claim 1, wherein the temperature-controlled fluid comprises a contrast agent visible through magnetic resonance imaging.

5. The method of claim 1, wherein infusing the bolus of the temperature-controlled fluid comprises infusing the bolus via a syringe pump.

6. The method of claim 1, further comprising graphically displaying the change in the temperature sensed by the at least one temperature sensor over a period of time.

7. The method of claim 6, wherein the period of time comprises about 10 seconds to about 300 seconds.

8. The method of claim 1, wherein positioning the distal end of the catheter at the location in the cerebrospinal fluid of the patient comprises positioning the distal end of the catheter at a plurality of locations in the cerebrospinal fluid of the patient, and wherein determining the flow rate of the cerebrospinal fluid comprises determining a respective local cerebrospinal fluid flow rate for each of the plurality of locations.

9. The method of claim 8, wherein outputting the indication of the estimated quality of the potential dispersion comprises producing a cerebrospinal-fluid-flow-rate heatmap of an intraspinal space of the patient.

10. A medical device comprising:
    a catheter having an elongated body comprising:
        a distal end configured to be positioned at a location within a flow of a cerebrospinal fluid of a patient;
        a proximal end, wherein the elongated body defines a lumen extending lengthwise from the proximal end to the distal end, the lumen being configured to deliver a bolus of a temperature-controlled fluid from the proximal end to an infusion port positioned in proximity to the distal end prior to a delivery of a medicament at the location within the flow of cerebrospinal fluid; and
    at least one temperature sensor positioned in proximity to the distal end of the catheter at a fixed distance from the infusion port, the at least one temperature sensor configured to generate temperature data indicative of a temperature of a mixture of the cerebrospinal fluid and the bolus of the temperature-controlled fluid; and
    a processor configured to:
        receive the temperature data sensed by the at least one temperature sensor over a period of time;
        determine, based on the temperature data, flow rate of the cerebrospinal fluid;
        determine, based on the flow rate of the cerebrospinal fluid, an estimated quality of a potential dispersion of the medicament into the cerebrospinal fluid by the catheter at the location; and
        output for display an indication of the estimated quality of the potential dispersion of the medicament at the location.

11. The medical device of claim 10, wherein the temperature-controlled fluid comprises a saline solution.

12. The medical device of claim 10, wherein the temperature-controlled fluid comprises a bolus temperature in a range of about 35° F. to about 46° F.

13. The medical device of claim 10, wherein the temperature-controlled fluid comprises a contrast agent visible through magnetic resonance imaging.

14. The medical device of claim 10, further comprising a syringe pump configured to inject the temperature-controlled fluid.

15. The medical device of claim 10, wherein the period of time extends from infusion of the bolus of the temperature-controlled fluid to an expiration of a predefined time duration.

16. The medical device of claim 10, wherein the period of time ranges from about 10 seconds to about 300 seconds.

17. The medical device of claim 10, further comprising a display screen configured to display a graphical plot of the temperature data sensed by the temperature sensor over the period of time.

18. The medical device of claim 10, wherein the at least one temperature sensor comprises a first temperature sensor and a second temperature sensor positioned on opposite sides of the infusion port, and wherein the processor is further configured to determine a flow direction of the cerebrospinal fluid based on the temperature data.

19. The medical device of claim 18, wherein the first temperature sensor is positioned proximally to the infusion port and the second temperature sensor is positioned distally to the infusion port, and wherein the processor is further configured to determine a flow direction of the cerebrospinal fluid based on the temperature data.

20. A non-transitory, computer-readable medium comprising instructions that, when executed by a processor, cause the processor to:

receive, from a temperature sensor positioned at a distal end of a catheter positioned at a location within a cerebrospinal fluid of a patient, temperature data over a period of time, the temperature data indicating a temperature of a mixture of the cerebrospinal fluid and a bolus of a temperature-controlled fluid infused into the cerebrospinal fluid via an infusion port at the distal end of the catheter;

determine, based on the temperature data, a flow rate of the cerebrospinal fluid;

determine, based on the flow rate of the cerebrospinal fluid, an estimated quality of a potential dispersion of a medicament into the cerebrospinal fluid via the distal end of the catheter at the location; and output, for display, an indication of the estimated quality of the potential dispersion of the medicament at the location.

* * * * *